United States Patent
Zadeh

(10) Patent No.: US 11,109,937 B2
(45) Date of Patent: Sep. 7, 2021

(54) INSTRUMENTS AND METHODS FOR SUBPERIOSTEAL TUNNELING AND RELATED SURGICAL PROCEDURES

(71) Applicant: Homayoun H. Zadeh, Woodland Hills, CA (US)

(72) Inventor: Homayoun H. Zadeh, Woodland Hills, CA (US)

( * ) Notice: Subject to any disclaimer, the term of this patent is extended or adjusted under 35 U.S.C. 154(b) by 0 days.

(21) Appl. No.: 16/247,473

(22) Filed: Jan. 14, 2019

(65) Prior Publication Data

US 2019/0216568 A1    Jul. 18, 2019

Related U.S. Application Data

(60) Provisional application No. 62/617,093, filed on Jan. 12, 2018.

(51) Int. Cl.
*A61C 8/00* (2006.01)
*A61B 90/00* (2016.01)
(Continued)

(52) U.S. Cl.
CPC .......... *A61B 90/08* (2016.02); *A61B 17/0469* (2013.01); *A61B 17/0482* (2013.01); *A61B 17/30* (2013.01); *A61B 17/32* (2013.01); *A61F 2/2803* (2013.01); *A61B 17/02* (2013.01); *A61B 2017/0046* (2013.01); *A61B 2017/00424* (2013.01); *A61B 2017/00738* (2013.01); *A61B 2017/2926* (2013.01); *A61B 2017/301* (2013.01); *A61B 2017/320056* (2013.01); *A61B 2090/0817* (2016.02); *A61B 2090/08021* (2016.02); *A61F 2002/4622* (2013.01)

(58) Field of Classification Search
CPC . A61B 90/08; A61B 17/0469; A61B 17/0482; A61B 17/0483; A61B 17/30; A61B 17/32; A61B 17/02; A61B 2090/08021; A61B 2090/0817; A61B 2017/00424; A61B 2017/0046; A61B 2017/00738; A61B 2017/2926; A61B 2017/301; A61B 2017/320056; A61B 2017/320044; A61F 2/2803; A61F 2002/4622
USPC .......... 600/210; 606/79, 148, 161, 170, 190, 606/205; 433/141
See application file for complete search history.

(56) References Cited

U.S. PATENT DOCUMENTS 99,050 A  *  1/1870  Battle .................. A61C 8/0089
                                                     433/165
906,085 A  *  12/1908  Tolman ............... A61F 2/30734
                                                     606/93

(Continued)

*Primary Examiner* — Eduardo C Robert
*Assistant Examiner* — David C Comstock
(74) *Attorney, Agent, or Firm* — Kurt T. Mulville; VLP Law Group, LLP

(57) ABSTRACT

The present invention is a group of surgical instruments with improved function and design for dental and craniofacial surgery, especially subperiosteal tunneling and related procedures. The instruments include surgical elevators for vestibular incision or incisions in the gingival sulcus. The instruments have varying angles and shapes to create a mucosal tunnel in any oral or maxillofacial region. The instrument suite also optionally includes specially designed forceps for introduction of graft material inside the subperiosteal tunnel and to assist with suturing of the graft to surrounding tissue.

10 Claims, 7 Drawing Sheets

(51) Int. Cl.
*A61B 17/04* (2006.01)
*A61F 2/28* (2006.01)
*A61B 17/30* (2006.01)
*A61B 17/32* (2006.01)
*A61B 17/29* (2006.01)
*A61F 2/46* (2006.01)
*A61B 17/00* (2006.01)
*A61B 17/02* (2006.01)

(56) References Cited

U.S. PATENT DOCUMENTS

| | | | | |
|---|---|---|---|---|
| D212,868 S * | 12/1968 | Olson | | A61C 1/084 |
| | | | | D24/147 |
| 4,044,770 A * | 8/1977 | Ocel | | A61B 17/320708 |
| | | | | 606/161 |
| 5,088,925 A * | 2/1992 | Mason | | A61H 39/04 |
| | | | | 433/141 |
| 5,188,531 A * | 2/1993 | Von Sutfin | | A61C 3/03 |
| | | | | 433/118 |
| 5,323,765 A * | 6/1994 | Brown | | A61B 17/320036 |
| | | | | 128/898 |
| 6,475,172 B1 * | 11/2002 | Hall | | A61B 17/24 |
| | | | | 601/137 |
| 8,061,372 B1 * | 11/2011 | Allen | | A61C 15/045 |
| | | | | 132/329 |
| 8,770,974 B2 * | 7/2014 | Suter | | A61C 8/0089 |
| | | | | 433/165 |
| 9,826,920 B2 * | 11/2017 | Pahuja | | A61F 11/006 |
| 2002/0151769 A1 * | 10/2002 | Kim | | A61B 17/02 |
| | | | | 600/210 |
| 2008/0071304 A1 * | 3/2008 | Tai | | A61B 17/00008 |
| | | | | 606/190 |
| 2011/0046631 A1 * | 2/2011 | Suter | | A61C 1/084 |
| | | | | 606/96 |
| 2012/0277761 A1 * | 11/2012 | Boling | | A61B 17/24 |
| | | | | 606/129 |
| 2015/0182210 A1 * | 7/2015 | Mayer | | A61F 2/30734 |
| | | | | 606/93 |
| 2016/0074135 A1 * | 3/2016 | Aboalshamat | | A61C 3/00 |
| | | | | 433/147 |
| 2016/0135921 A1 * | 5/2016 | Gordon | | A61C 1/12 |
| | | | | 433/140 |
| 2016/0166276 A1 * | 6/2016 | Huang | | A61B 17/1644 |
| | | | | 606/169 |
| 2017/0296308 A1 * | 10/2017 | Lee | | A61C 8/0089 |
| 2017/0319298 A1 * | 11/2017 | Lee | | A61C 8/0089 |
| 2018/0110584 A1 * | 4/2018 | Bettens | | A61C 8/0089 |
| 2018/0368875 A1 * | 12/2018 | Castillo | | A61B 17/32 |
| 2019/0090868 A1 * | 3/2019 | Bracy | | A61B 17/0469 |

* cited by examiner

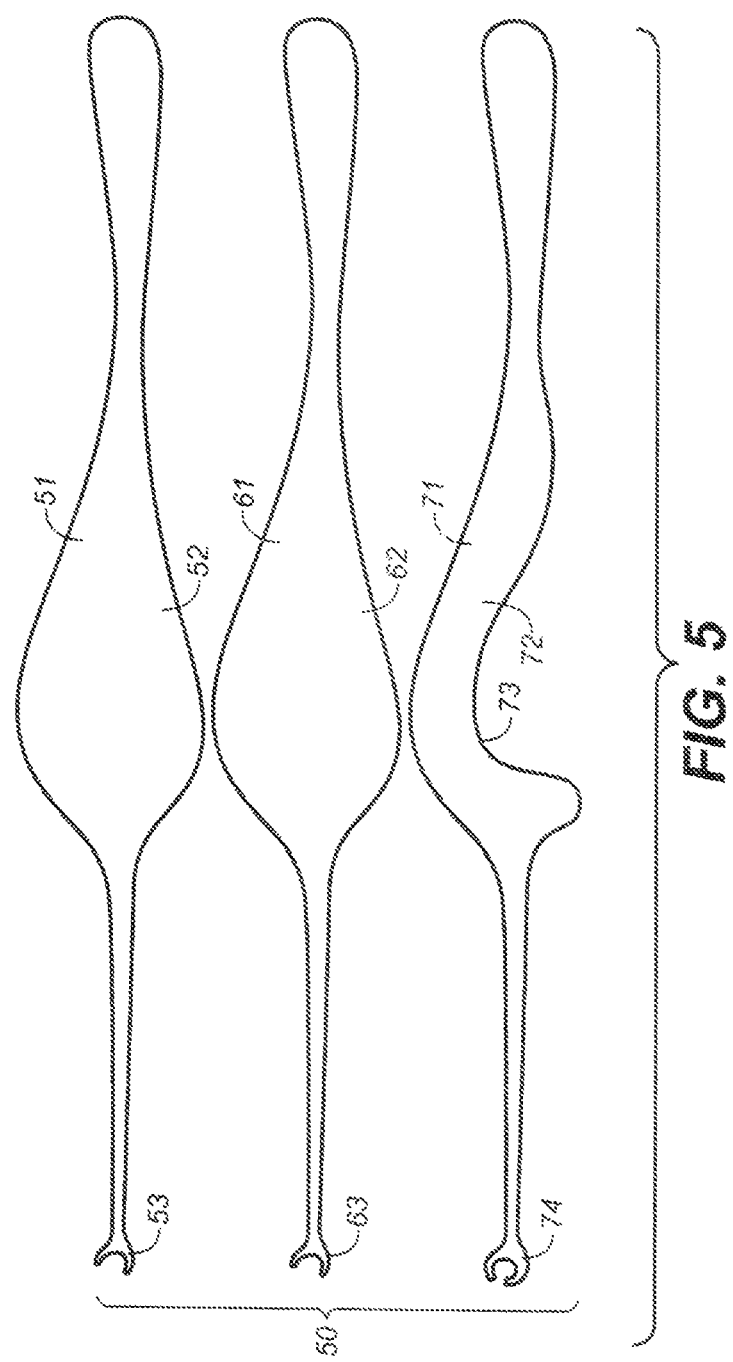

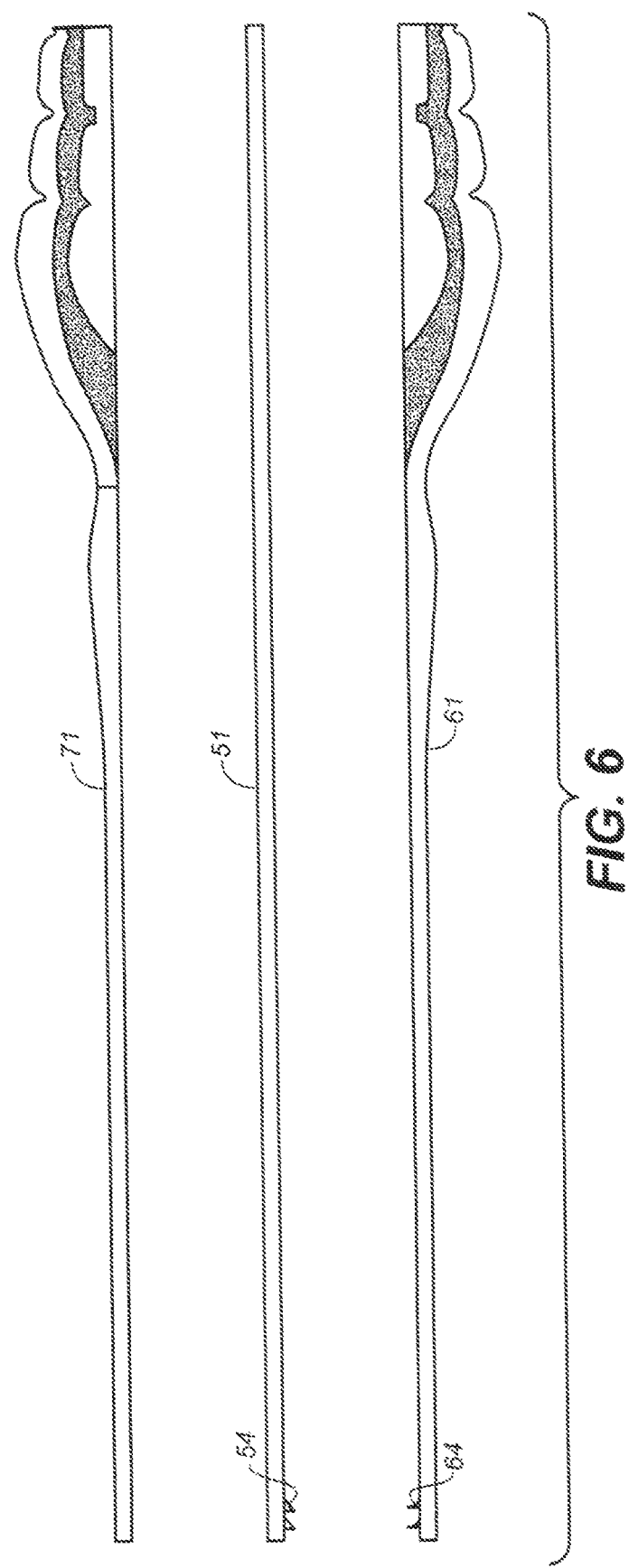

INSTRUMENTS AND METHODS FOR SUBPERIOSTEAL TUNNELING AND RELATED SURGICAL PROCEDURES

CROSS REFERENCE TO RELATED APPLICATIONS

This application is related to and claims priority of U.S. provisional application ("Provisional Application"), Ser. No. 62/617,093, filed Jan. 12, 2018, entitled "Instruments and Methods for Subperiosteal Tunneling and Related Surgical Procedures." The priority of this application is expressly claimed, and the disclosure is hereby incorporated by reference in their entirety.

BACKGROUND OF THE INVENTION

Mucosal surgery operations are common to treat dental and craniofacial disorders. Traditionally, mucosal surgical procedures require large incisions and reflection of a region of tissue called the mucoperiosteal flaps. These large flaps contain the vascular supply and are crucial to maintain the health of the mucosal tissue and surrounding structures. Large incisions and pronounced reflection of mucoperiosteal flaps cause delayed healing, excessive pain, inflammation, and the potential for edema. Traditional mucoperiosteal flap procedures often produce unsatisfactory results because of scar formation and negative aesthetic consequences. Moreover, the healing pattern can be unpredictable and lead to excess scar tissue, gingival recession, necrosis, and other negative outcomes.

For these reasons, procedures that enable minimally invasive tunneling through mucosal tissue have been proposed as a way of reducing surgical trauma from conventional flap surgery. Tunnel surgery includes making a much smaller incision at an access site remote from the therapeutic target. Once the precise access incision away from the target site is made, the surgeon creates a submucosal tunnel to access the tissue and bone at the surgical site. Once the incision and submucosal tunnel are made, access is obtained by introducing a range of instruments through the incision, traversing the length of the submucosal tunnel, and bringing the functional ends of the instruments to the target therapeutic area.

Subperiosteal tunnel surgery can be performed through several routes and methods. The access for the tunnel can be made through either the gingival sulcus or through a vestibular incision. A gingival sulcular tunnel has the disadvantage of limited access through the very small gingival sulcus. In particular, in the presence of exostosis, the sulcular tunnel route is very challenging to the surgeon. Vestibular access offers a much wider access area, which is technically easier but still requires specialized instrumentation to perform the surgical procedure while reducing trauma to the surrounding tissues. There are broadly two kinds of tunnel, namely subperiosteal (full-thickness) and supra-periosteal (split- or partial-thickness) tunnel. Supra-periosteal tunnel requires sharp dissection, while subperiosteal tunnel requires blunt dissection. In order to efficiently perform subperiosteal tunneling, mucoperiosteal complex has to be elevated from underlying bone.

Although clear advantages of this surgical technique exist, such procedures are very challenging for the surgeon because the entire surgery has to be performed through the small access incision. Therefore, these procedures would be improved and be more widely practices if specialized instruments were developed that allow efficient separation of tissue from bone and elevation of tissue to create a submucosal tunnel allowing the introduction of other therapeutics instruments while minimizing trauma.

SUMMARY OF THE INVENTION

The present invention is a suite of instruments for improved subperiosteal tunneling procedures and improved methods for dental and craniofacial surgery.

The elevator devices of the invention have a number of structural and operational features that yield unique advantages for mucoperiosteal complex reflection, including but not limited to the following:

1) the elevators feature an atraumatic flat tip to provide increased contact between elevators and bone;
2) the elevators feature atraumatic rounded edges around the periphery and at the distal edge of the flap tips. These structures allow the tips to be slightly rotated to activate a narrower tip, when necessary;
3) the tips of the elevators have a pre-determined curve designed to engage bone along a length of the tip to avoid puncturing the overlying mucosal tissue;
4) the elevators have an anodized dark color, which facilitates visualization of the instrument through the tissue when introduced through the tunnel; and
5) the elevators preferably have curved shanks with specific at predetermined portions along their length angulations to facilitate access to surgical areas; and
6) the handles of the elevators have an ergonomic design allowing the surgeon to easily manipulate the instruments by hand during a procedure.

Specially designed graft placement forceps have a number of features that facilitate minimally invasive, atraumatic introduction and placement of a graft though the tunnel. The graft forceps have a number of structural and operational features that yield unique advantages for graft placement, including but not limited to the following:

1) the forceps have exactly three prongs. Two grasping prongs are actuated by hand to grasp the graft and inserted the graft inside the tunnel. The third alignment prong aligns with the first two prongs but is positioned over the exterior of the tunnel. At least one and preferably all three of these three prongs have a semi-circular eyelet at the tip for passage of suture and needle. The tips align while simultaneously holding the graft in position inside the tunnel. Once the graft is in position a suture needle is passed through the surface mucosal flap, as well as the graft to allow suturing the graft to the flap.
2) The two grasping prongs each have teeth at the tip strategically aligned and oriented away from the tip. This design allows the graft being grasped by the pair of tips to be inserted inside the tunnel and to remain securely held during insertion. The orientation of the teeth also allows the forceps to be retracted out of the tunnel and without displacing the graft during removal of the forceps.
3) The forceps handles are designed to allow the surgeon to press together only the first pair of prongs to hold the graft without actuating the third handle, whose entire length remains outside of the tunnel. Once the graft is positioned in place, the third handle is actuated to bring the tip in contact with the exterior of the tissue, aligned with the distal tip of the other two prongs. This allows alignment of the three eyelets together, while holding the graft inside the tunnel. The aligned eyelets at the tips can are then used to pass a suture through the surface mucosa and through the graft to attach the graft to the mucosa.

The methods of the invention include introducing the unique elevators through the vestibule to efficiently perform subperiosteal tunneling procedures including the elevation of the mucoperiosteal complex from underlying bone. The methods also include use of the 3-prong forceps of the invention to introduce a graft through a minimally invasive incision, advancing the graft to a target site, and graft placement. The methods include using any of the unique devices of the invention to perform a surgical procedure, including but not limited to at the gingival margins to alleviate a diseased condition.

DESCRIPTION OF THE FIGURES

FIG. 5 is an embodiment of the three-prong forceps of the invention showing the three individual handles having an eyelet at the distal tip thereof.

FIG. 6 is a side view of the three-prong forceps of the invention showing an orientation of the distal end of the forceps wherein a pair of the grasping prongs feature forward directed teeth for graft engagement and positioning, combined with atraumatic removal of the forceps, together with an alignment prong.

DETAILED DESCRIPTION OF THE INVENTION

Figure 1A:
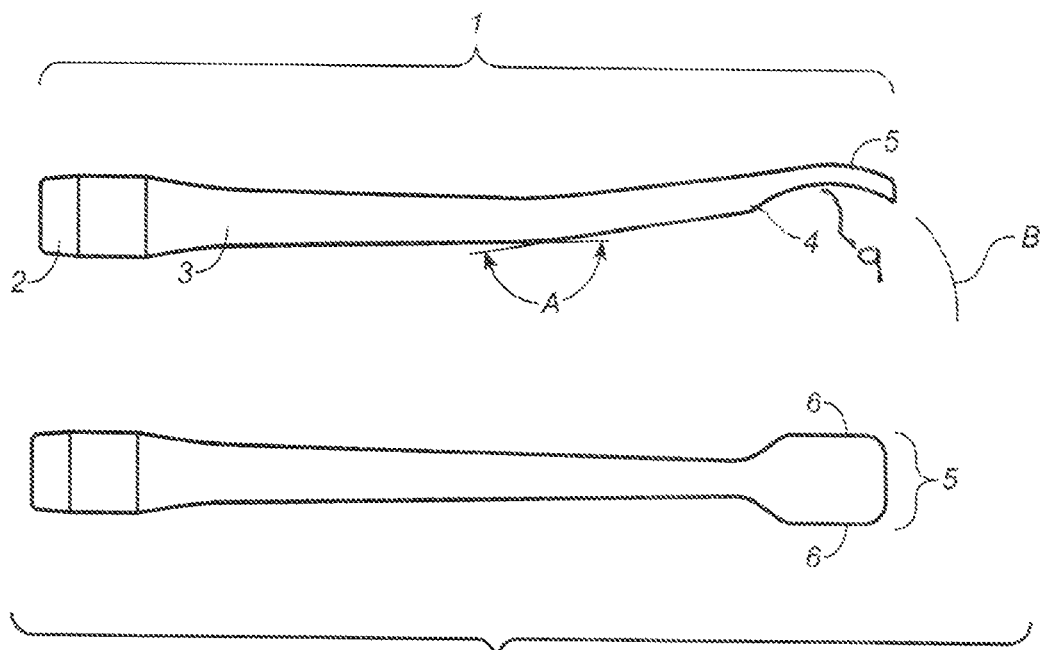
FIGS. 1A and 1B are an embodiment of the elevators of the invention having a first elongated shaft region and a second elongated shaft region oriented at an angle to one another and terminating in a curved atraumatic tip.
Figure 1B:
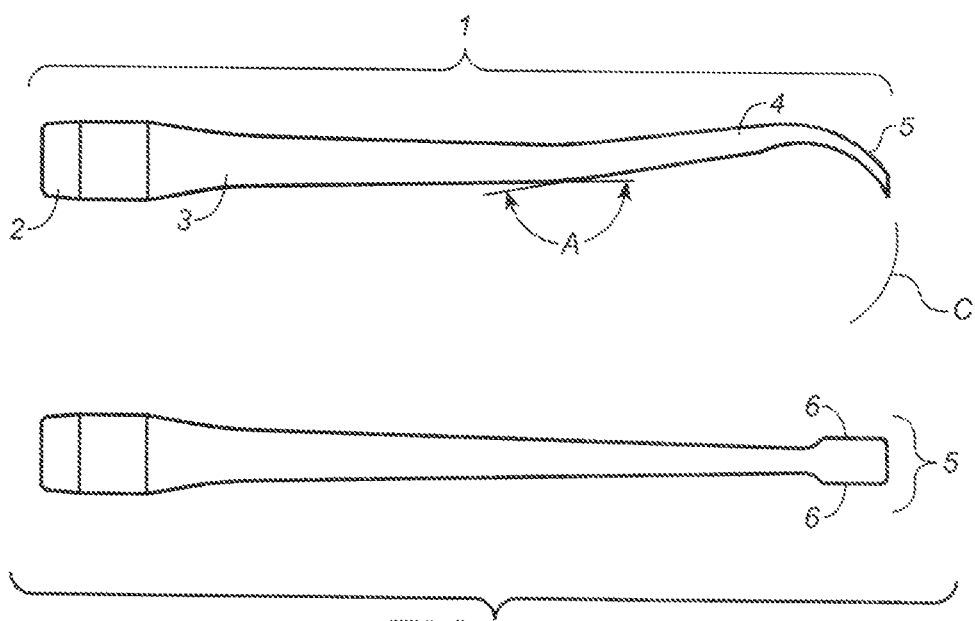

Referring to FIG. 1A, the elevator 1 is comprised of a base portion 2 that is comprised of a handle 2 or has a mating fixture (not shown) for attachment to a separate, reusable handle feature preferably having an ergonomic grip. The elevator 1 has a first elongated shaft region 3 and a second elongated shaft region 4 wherein the first and second elongated shaft regions are oriented by angle A having a range between 0° and 45° and terminate in a distal curved atraumatic tip 5. The outer edge 6 of the atraumatic tip 5 is rounded and curved to atraumatically engage tissue during a tunneling procedure. The distal end of the elevator 1 is comprised of an arc region 9 that terminates in the atraumatic tip 5. As is apparent from the side view of FIG. 1A, the atraumatic tip 5 is angled and curved relative to the second elongated shaft region 4 as indicated by the measurement of arc B. Arc B is preferably one-quarter circle but may range from a one-eighth circle to a one-half circle. The embodiment of FIG. 1B is similar to the embodiment of the elevators of FIG. 1A, but having an altered size of the distal atraumatic tip 5 for a different surgical application including altered lengths of the first elongated shaft region 3 and the second elongated shaft region 4. The embodiment of FIG. 1B, has a similar angle A reflecting the deflection of the first elongated shaft 3 relative to the second elongated shaft 4 and an extended arc region 9 as indicated by the arc measure C.

Figure 2:
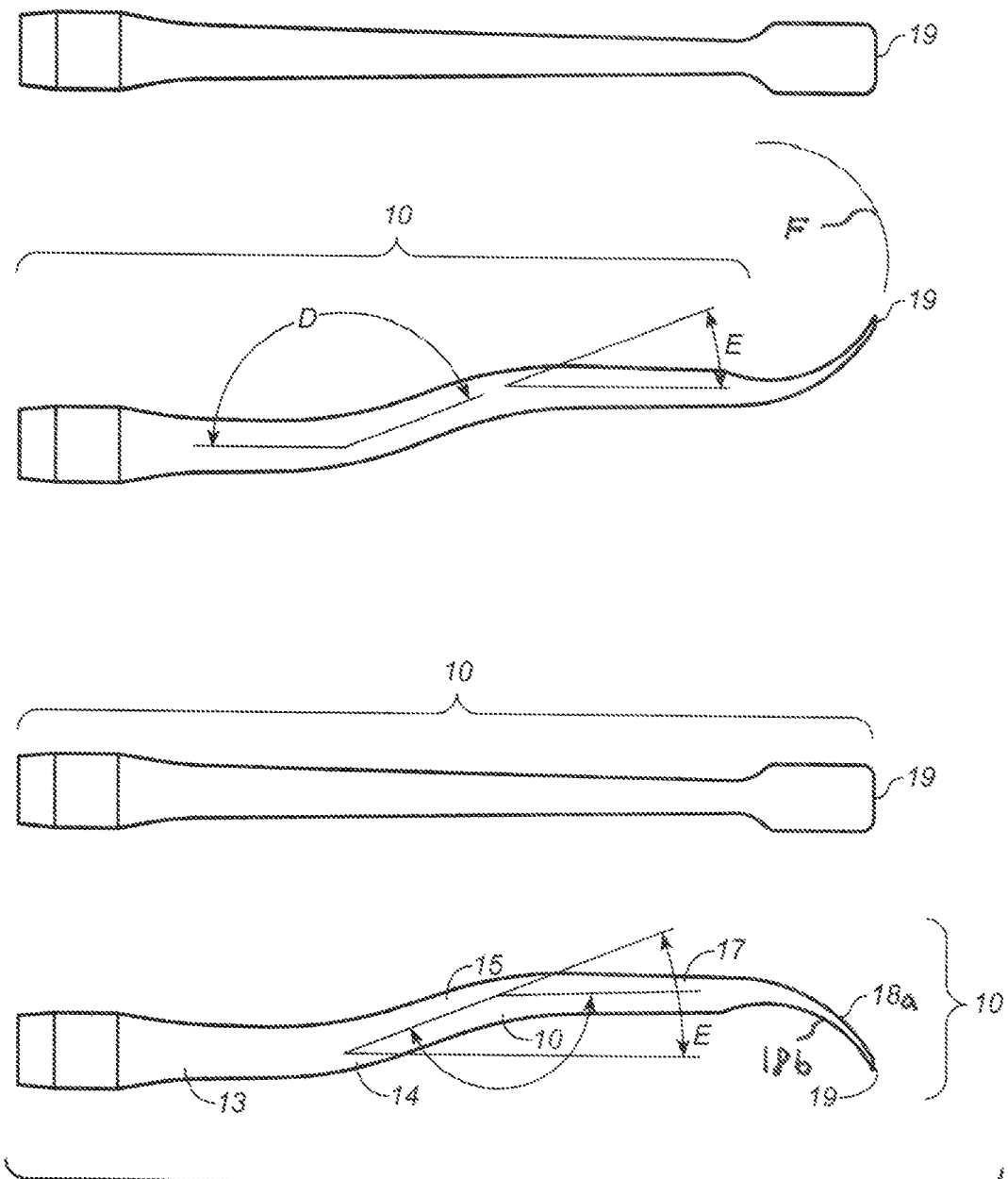
FIG. 2 is an embodiment of an elevator of the invention having a first elongated shaft, a curved transitional portion to a second shaft region and optionally a second curved transitional portion and terminating in a curved atraumatic tip.

Referring to FIG. 2, an elevator of the invention 10 having handle 12 also has a mating fixture (not shown) for attachment to a separate, reusable handle feature preferably having an ergonomic grip. The elevator 10 has a proximal shaft region 13, a curved transitional portion 14 connected to a second distal shaft region 15 and optionally a second curved transitional portion 16 operably connected to a distal shaft region 17 and terminating in a curved atraumatic tip 18a. The first and second shaft regions 13, 15 are oriented by angle D having a range between 0° and 45° and the second shaft region 15 is oriented to the first shaft region 13 by angle E also having a range between 0° and 45°. In one embodiment the sum of angles D and B is approximately 180°. As with the embodiment of FIGS. 1A and 1B, the elevator terminates in an atraumatic tip 19 having a distal edge that is rounded and curved for atraumatic engagement of tissue during a tunneling procedure.

The distal end of the elevator 1 is comprised of an arc region 18b that terminates in the atraumatic tip 19. As is apparent from the side view of FIG. 2, the atraumatic tip 19 is angled and curved relative to the second distal shaft region 4 as indicated by the measurement of arc F. Arc F is preferably one-quarter circle but may range from a one-eighth circle to a one-half circle. The embodiments of FIG. 2 are similar to the embodiment of the elevators of FIGS. 1A, 1B but having an altered size of the distal atraumatic tip 19 for a different surgical application including altered lengths of the first proximal shaft region 13 and the second distal shaft region 17. The embodiment of FIG. 1B, has a similar angle A reflecting the deflection of the first elongated shaft 3 relative to the second elongated shaft 4 and an extended arc region 18b indicated by the arc measure F.

Figure 3A:
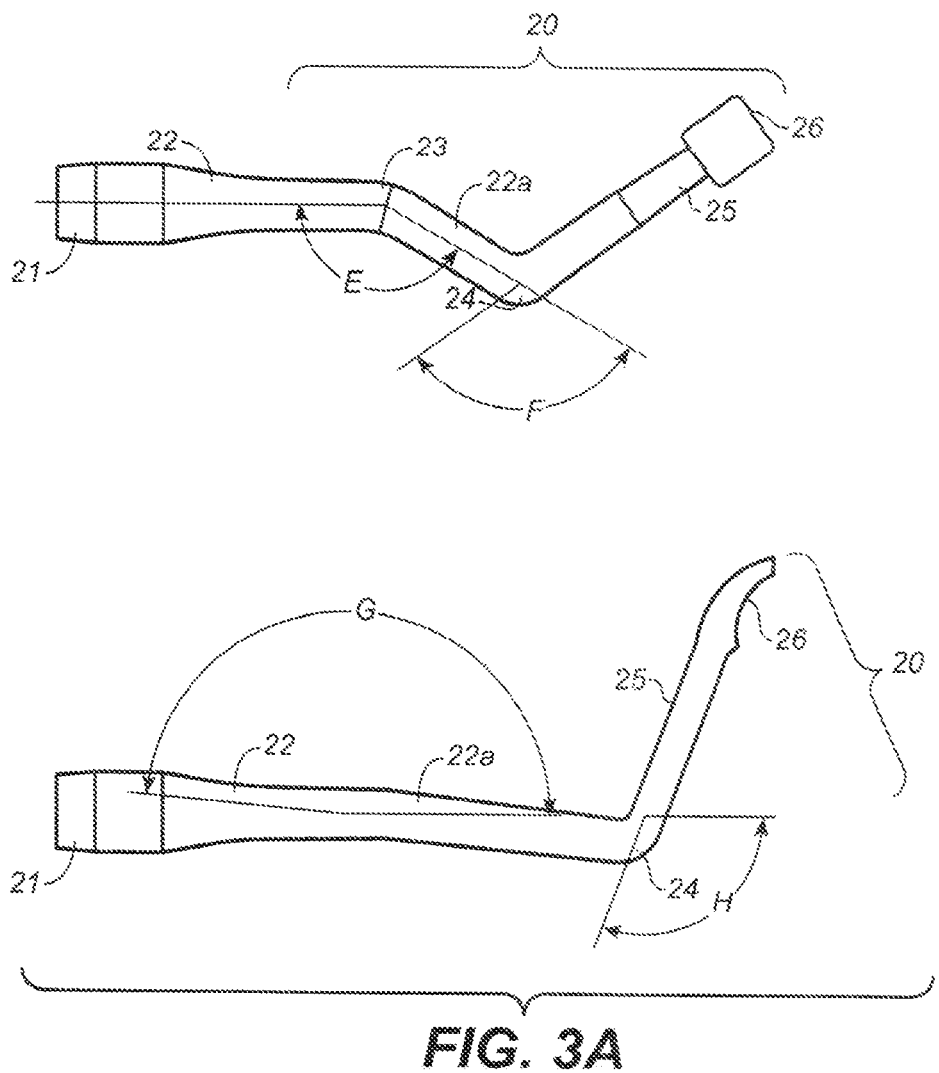
FIGS. 3A and 3B are embodiments of the elevator of the invention having first, second, and third elongated shaft regions oriented at predetermined angles to one another and to a handle for positioning of a curved atraumatic tip at a surgical site.
Figure 3B:
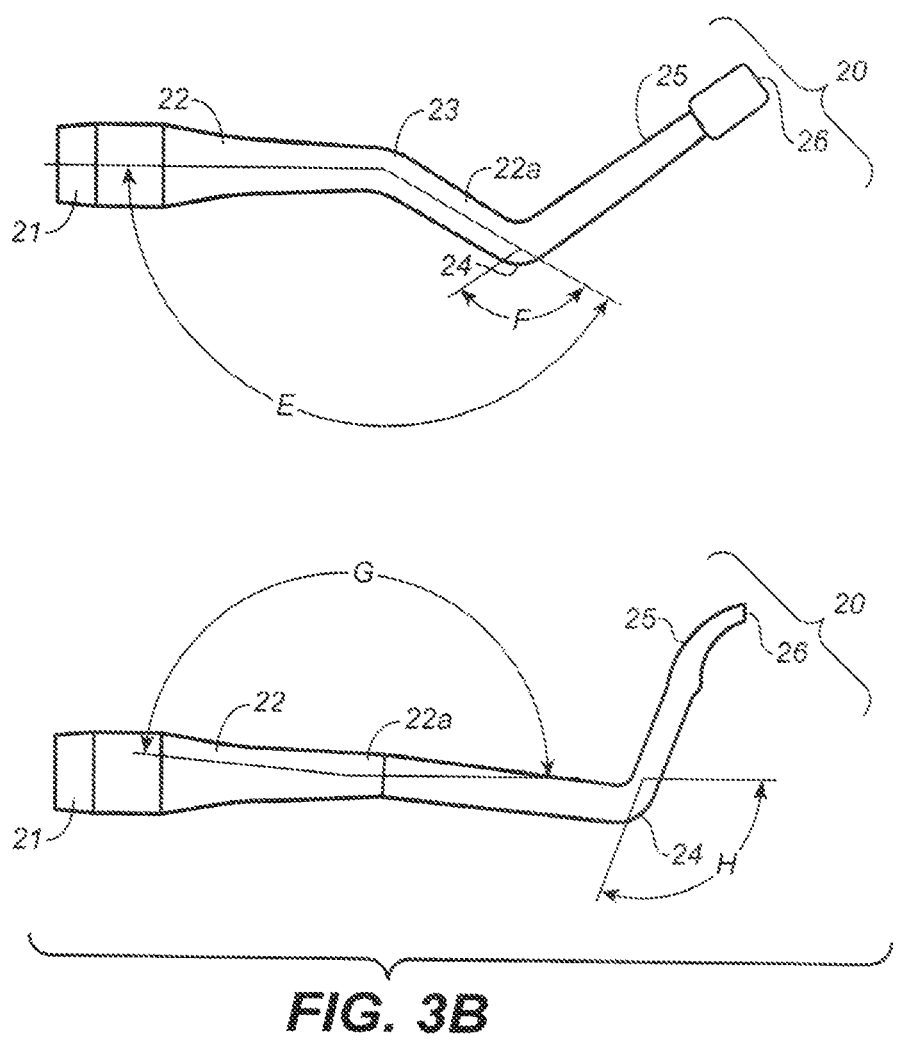

Referring to FIG. 3A, an elevator embodiment of the present invention 20 has a base portion 20, a first elongated shaft region 22, a first angle 23, a second elongated shaft region 22 a, a second angle 24, and a third shaft region 25 that orients distal atraumatic tip 26 at a predetermined angle relative to the normal line traversing the base portion 21 and the length of the first shaft region 22. The first and second shaft regions 22, 22a are oriented around angle E (between 0° and 45°) and the second and third shaft regions 22a, 25 or oriented around angle F preferably greater than 90° and less than 180°) to achieve the desired positioning of the atraumatic tip 26. In the second embodiment of FIG. 3B (lower, the first shaft region 22 and the second shaft region 22 a are oriented around angle G and the second shaft region 22 a and the third shaft region 25 are oriented around angle H. As with the prior embodiments, the atraumatic tip terminates in an outer edge that is rounded and curved to be atraumatic to surrounding tissue during a tunneling procedure. Referring to FIG. 3B, a similar embodiment to the elevator of FIG. 3A is shown having different dimensions and a similar set of angular orientations, shaft regions and distal tip.

Figure 4A:
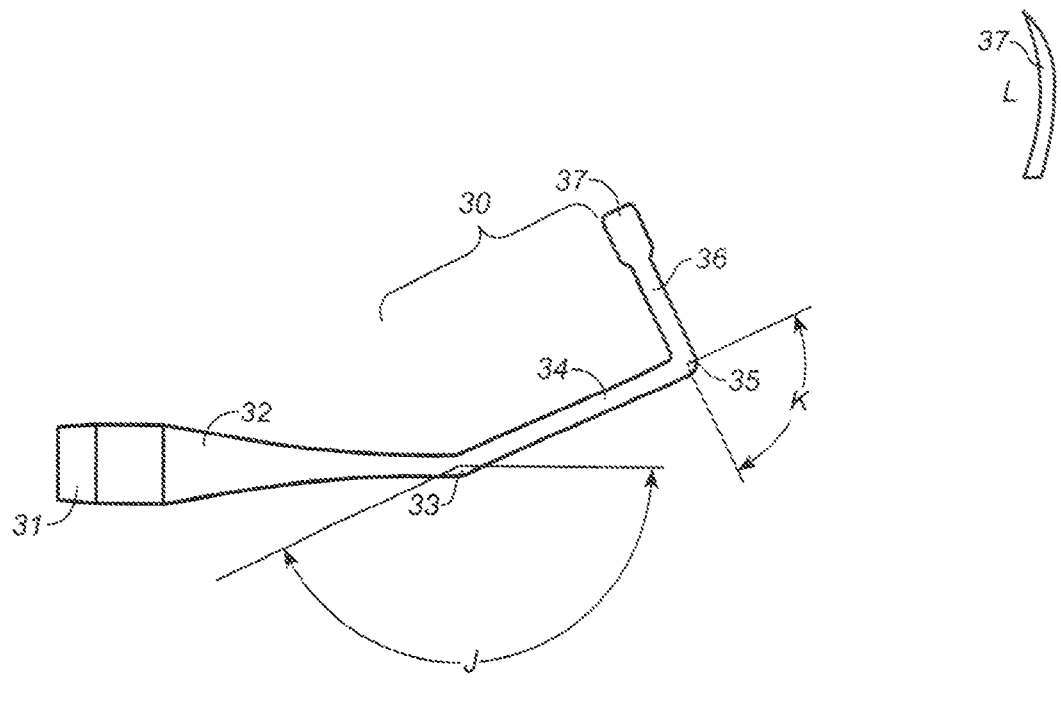
FIG. 4A and FIG. 4B are embodiments of the elevator of the invention having three elongated shaft regions disposed in three different planes to permit advantageous orientation of a distal tip thereof at a surgical site.
Figure 4B:
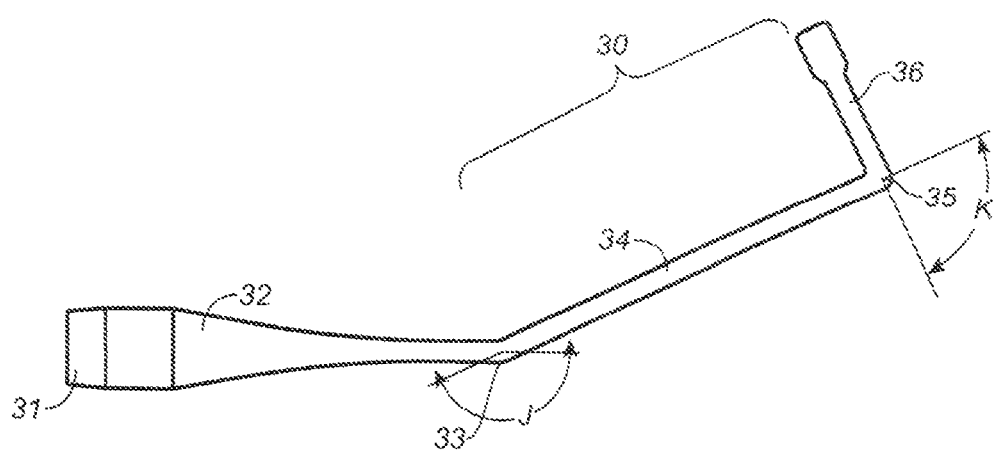

Referring to FIGS. 4A and 4B, elevators of the present invention may employ distinct shaft regions that are oriented in different planes to position the atraumatic tip advantageously at the surgical site once introduced through an incision. Referring to FIGS. 4 A, 4B, the base portion 31 is adjacent to first shaft region 32 that is at an angle J relative to the second shaft region 34 around junction 33 that also establishes a first plane in which both of the first shaft region 32 and second shaft region 34 are disposed. Junction 35 orients the third shaft region 36 at angle K relative to the second shaft region 34 and also orients the third shaft region 36 out of the plane in which the first and second shaft regions 32, 34 are contained. A different alternative would be to orient second shaft region 34 and third shaft region 36 in the same plane while orienting the base portion 31 in the first shaft region 32 in a separate plane relative to the plane containing the second and third shaft regions 34, 36. As with the embodiments described above, the third shaft region 36 terminates in an atraumatic tip 37 having the characteristics described above. As with the foregoing embodiments, the atraumatic tip 37 may be curved along its length by arc L.

FIG. 5 is an embodiment of the three-prong forceps of the invention showing the three individual handles having an eyelet at the distal tip thereof. Referring to FIG. 5, the individual prongs 51, 61, 71 are shown separately and detached to illustrate the differing shapes of the pair of grasping prongs 51, 61 and the alignment prong 71. Each prong 51, 61, 71 is comprised of a handle portion 52, 62, 72 for operation by the hand of the surgeon. In a preferred embodiment, the hand portion 52, 62 of the pair of grasping prongs 51, 61 have a similar shape for ease of operation. The handle portion 72 of the alignment prong 71 has a different shape, optionally effected by a cutout portion 73 of the alignment prong 71 relative to the handle portion 52, 62 of the grasping prongs 51, 61.

The distal end of each prong features a suture guide, 53, 63, 74 for alignment when the forceps are actuated by hand. In a preferred embodiment, the suture guide is a semicircular eyelet 53, 63, 74 such that the suture guide portions are in alignment during operation of the forceps. As described above, the pair of grasping prongs 51, 61 engage a graft at the distal tip thereof proximate to the suture guide and are held in close conformity to introduce the guide through a minimally invasive incision. The alignment probe 74 remains outside the incision and is brought into conforming engagement on the opposite side of the mucosal tissue to provide for accurate placement of a suture to attach the graft to the mucoperiosteal flap.

FIG. 6 is a side view of the three-prong forceps 50 of the invention showing an orientation of the distal end of the forceps 50 wherein the pair of the grasping prongs 51, 61 feature forward directed teeth 54, 64 for graft engagement and positioning. In use, the pair of teeth 54, 64 engage the graft and hold the graft firmly in position relative to the length of the forceps during graft introduction. Following suture of the graft to the mucoperiosteal flap, the three-prong forceps 50 are atraumatically removed leaving the graft securely in place.

While the present invention has been particularly shown and described with respect to certain preferred and illustrative embodiments, it will be understood by those skilled in the art that variations and modifications may be made therein without departing from the spirit and scope of the present invention.

What is claimed is:

1. A suite of surgical instruments for subperiosteal tunneling comprising:
   a first elevator having a base portion comprised of a handle having an ergonomic grip, a first elongated shaft region, a second elongated shaft region and terminating in a distal curved and rectangular atraumatic tip;
   a second elevator having an ergonomic grip, a first elongated shaft region, a second shaft region having a curved transitional portion and terminating in a distal curved atraumatic tip, wherein a combination of an angled portion of the first elongated shaft region and a second curved transitional portion and the second shaft region have positive values for at least two angles along the length of the second elevator such that the distal curved atraumatic tip is comprised of an arc region that disposes a most distal portion of the distal tip outside an axis of the first elongated shaft region; and
   a third elevator having an ergonomic grip, and first, second, and third shaft regions having an angled portion therebetween such that the third shaft region has an angled portion relative to the first shaft region greater than 90° and less than 180°.

2. The suite of surgical instruments of claim 1 wherein the first, second, or third elevators is further comprised of a mating fixture.

3. The suite of surgical instruments of claim 1 wherein the first and second elongated shaft regions of the first elevator are oriented by angle having a range between 0° and 45°.

4. The suite of surgical instruments of claim 1 wherein at least a portion of any shaft region of the first, second, or third elevator is comprised of an anodized dark color for visualization through tissue.

5. The suite of surgical instruments claim 1 wherein the distal curved atraumatic tip of the first elevator is comprised of an arc region.

6. The suite of surgical instruments of claim 5, wherein the arc region of either the first or the second elevator is contiguous with the second shaft region.

7. The suite of surgical instruments of claim 5, wherein the arc region of the first or second elevator is between approximately one-eighth circle and approximately one-half circle.

8. The suite of surgical instruments of claim 1 wherein the third elevator is comprised of a distal atraumatic tip proximate to the third shaft region.

9. The suite of surgical instruments of claim 1 wherein the first and second shaft regions of the third elevator are disposed in a first plane and the third shaft region is disposed in a second plane.

10. The suite of surgical instruments of claim 1, wherein the first shaft region of the third elevator is disposed in a first plane and the second and third shaft regions of the third elevator are disposed in a second plane.

* * * * *